United States Patent [19]
Lefebvre

[11] Patent Number: 5,810,874
[45] Date of Patent: Sep. 22, 1998

[54] TEMPORARY FILTER CATHETER

[75] Inventor: Jean Marie Lefebvre, Lille, France

[73] Assignee: Cordis Corporation, Miami Lakes, Fla.

[21] Appl. No.: 787,552

[22] Filed: Jan. 22, 1997

[30] Foreign Application Priority Data

Feb. 22, 1996 [NL] Netherlands .......................... 1002423

[51] Int. Cl.⁶ .................................................. A61M 29/00
[52] U.S. Cl. ............................................ 606/200; 128/899
[58] Field of Search ............................... 606/1, 108, 191, 606/194, 198, 200; 623/1, 12

[56] References Cited

U.S. PATENT DOCUMENTS

| | | |
|---|---|---|
| 3,952,747 | 4/1976 | Kimmel, Jr. . |
| 4,969,891 | 11/1990 | Gewertz .................................. 606/200 |
| 5,152,777 | 10/1992 | Goldberg et al. ........................ 606/200 |
| 5,222,971 | 6/1993 | Willard et al. ........................... 606/200 |

FOREIGN PATENT DOCUMENTS

| | | |
|---|---|---|
| 0 437 121 A2 | 7/1990 | European Pat. Off. . |
| 2580504 | 10/1986 | France .................................... 606/200 |
| 2 606 642 A1 | 11/1986 | France . |
| 2 652 267 A1 | 9/1989 | France . |
| 2 696 092 A1 | 9/1992 | France . |

*Primary Examiner*—Michael Buiz
*Assistant Examiner*—William Lewis
*Attorney, Agent, or Firm*—Paul A. Coletti

[57] ABSTRACT

The invention relates to a filter catheter. This catheter comprises a tube-like basic body with a proximal and a distal end, a filter element arranged at the distal end formed by a number of strips arranged spaced out around the circumference, which are connected with both ends to the basic body. The relatively distal ends of the strips are connected in a detachable manner to the basic body by connecting member.

7 Claims, 2 Drawing Sheets

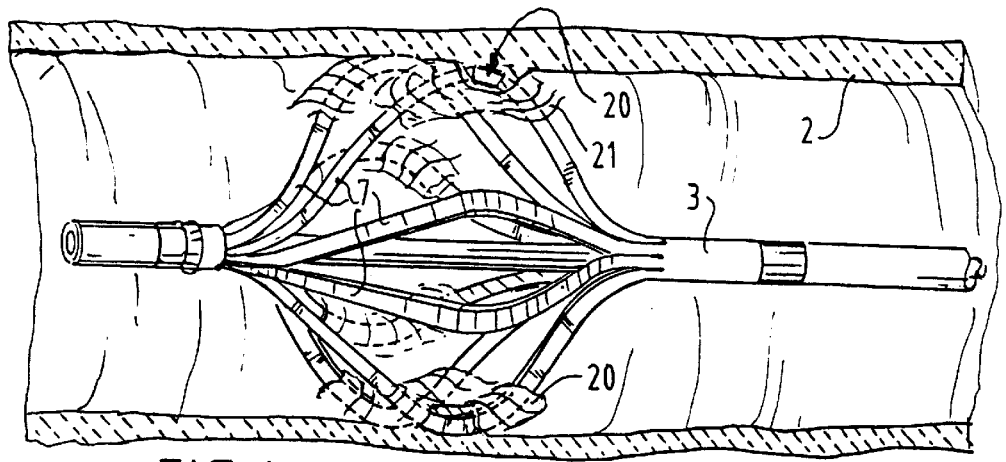
FIG.4
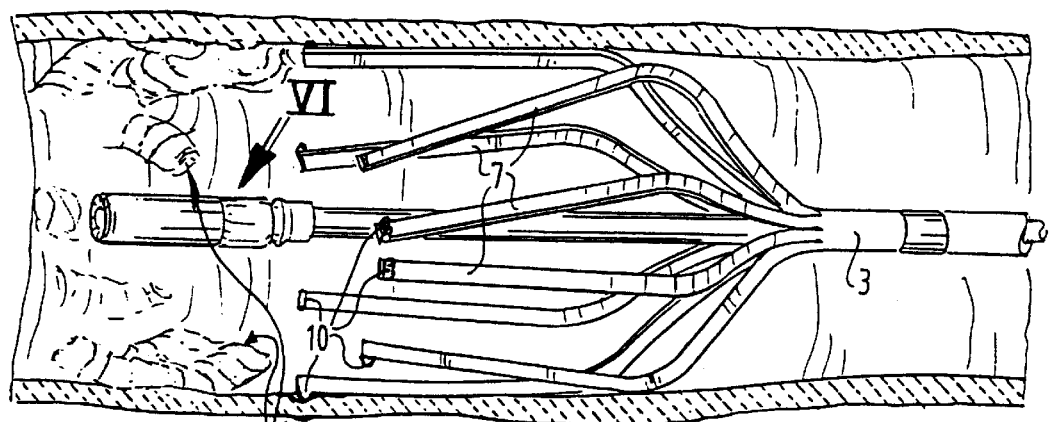
FIG.5
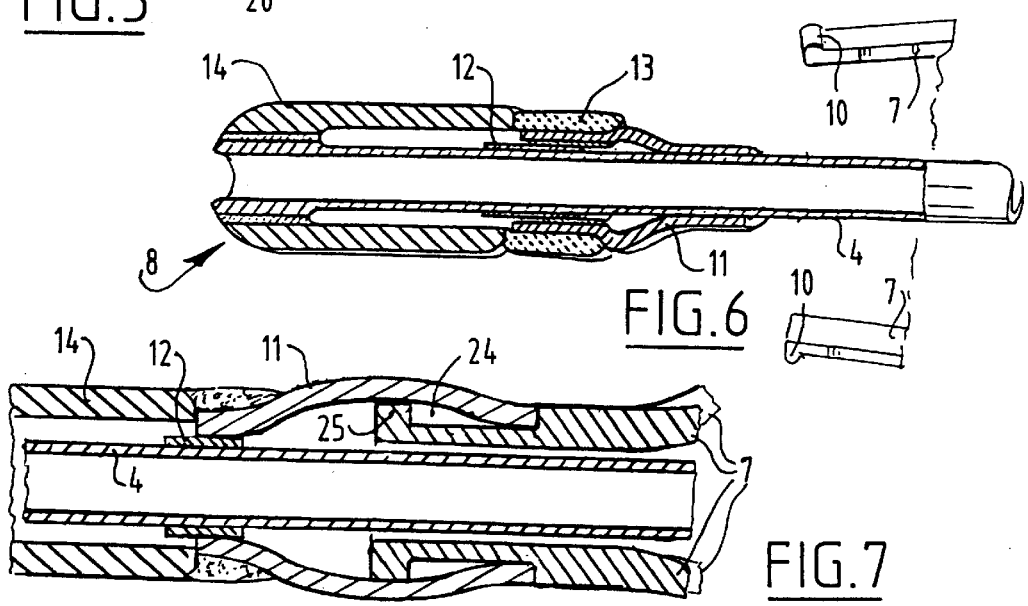
FIG.6
FIG.7

TEMPORARY FILTER CATHETER

BACKGROUND OF THE INVENTION

The invention relates to a temporary filter catheter such as used for instance during thrombolytic treatment. In that case the filter is arranged inside the vena cava and prevents blood thrombi from circulating freely through the vascular system and finishing up in places which could endanger the health of the patient.

For a certain group of patients, for whom such interventions entail a high degree of risk, it may be necessary to keep such a catheter for a longer period of time, for instance for a period of more than 10 days, in place.

Commonly used filter catheters of this type comprise, arranged at a distal end of a tube-like basic body, a filter element which is made up of a number of strips arranged spaced out around the circumference and connected to the basic body, which strips can be bent outwards by moving the opposite ends towards each other in order to be brought into the operative state by doing so the filter element grows into the tissue. Thus, the maximum period such filter catheters can stay inside the body is limited by the fact that the tissue of the wall of the blood vessel encapsulate the strip-shaped elements. The filter element grows into the tissue. Consequently such a filter can only be removed by potentially damaging the tissue.

SUMMARY OF THE INVENTION

The object of the invention is to provide a filter catheter which can stay for a long period of time inside the body of the patient.

With the filter catheter according to the invention this object is achieved because the relatively distal ends of the strips which define the filter element are connected with the basic body of the catheter by use of detachable connecting. On removing the catheter, the distal ends of the strips are disconnected, after which the filter element can be withdrawn, without damaging the tissue. On withdrawal, the strips slide through the 'channels' which have been formed in the tissue surrounding the strips.

Disconnecting the distal ends of the strips can be done by displacing an inner tube-like body contained in the catheter, in relation to the outer tube-like body of the catheter, by movement in a distal direction. By doing so a tensile force is applied to the strips consequently detaching them from the connecting means. As long as a certain minimum tensile force is not applied to the strips, the sleeve retains the distal ends of the strips. As soon as this minimum tensile force is exceeded, the ends of the strips will slide from under the sleeve so that they are detached from the connecting means.

Preferably, an additional measure as set out herein is employed. The ends of the strips are secured elastically, so that a reliable connection is maintained until the moment the connection to the catheter has to be broken. Because of the elasticity of the sleeve, the disconnecting force can be administered easily and accurately.

DESCRIPTION OF THE DRAWINGS

The invention will be explained in greater detail in the following detailed description with reference to the attached drawings.

FIG. 4 shows a view corresponding to FIG. 3 after a relatively long stay inside the body of the patient, and where the strips are grown into the tissue;

FIG. 5 illustrates the removal of the filter after disconnecting the ends of the strips;

FIG. 6 shows a view corresponding to FIG. 2 with the ends of the strips of the filter element detached; and FIG. 7 illustrates an alternative embodiment of connecting means for a catheter according to the invention.

DETAILED DESCRIPTION OF THE INVENTION

Figure 1:
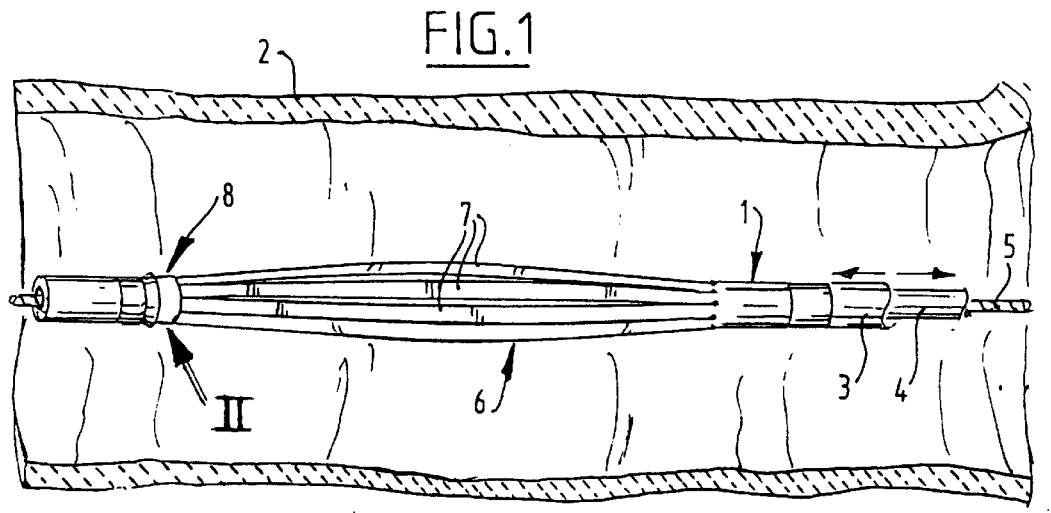
FIG. 1 shows the distal end of an example of an embodiment of a catheter according to the invention during the introduction thereof.

In FIG. 1 the distal end-section of a catheter 1 according to a preferred embodiment of the invention is shown. The catheter 1 has been introduced into a blood vessel 2 of a patient and the filter element 6 of this catheter still has to be unfolded in order to be able to carry out the filter function.

The catheter 1 comprises an outer tube-like body 3 inside of which an inner tube-like body 4 has been received in a movable manner. The inner tube-like body has a lumen through which a guide wire 5 extends when positioning the catheter and in particular the filter element 6 thereof.

In the case of the example of this preferred embodiment the filter element 6 is formed by a number of strips, which are made up of sections of the wall of the outer tube-like body 3, which are separated from one another by longitudinal cuts.

The relatively proximal ends of the strips 7, that is to say the ends of these strips on the right-hand side as seen in FIG. 1, form a hole with the outer tube-like body 3.

The relatively distal ends 10 of the strips 7 are connected to the inner tube-like element in a detachable manner by connecting means 8. The connecting means 8 retain the distal ends 10 of the strips 7 by means of a clamping connection. This clamping connection is obtained because the connecting means 8 comprise a sleeve 11 made of an elastic material, for instance silicone rubber.

The sleeve 11 has been fixed to the catheter by means of a layer of cured plastic material 13, for instance a cured epoxy. The end-section 14 of the catheter 1 has preferably been made of a soft material in order to achieve a maximum atraumatic action when introducing the catheter.

Figure 2:
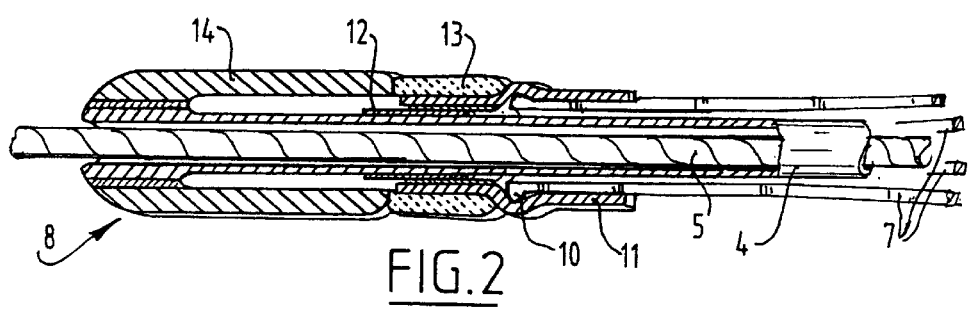
FIG. 2 shows a detailed view cut through at the arrow "II" of FIG. 1.

As can been seen in FIG. 2, a marking ring 12 has been arranged around the inner tube-like body 4 and a second marking ring has been arranged around the outer tube-like body 3. Both rings have for instance been made of gold to make the position of the filter element clearly visible on an X-ray screen in a catheterization laboratory.

Figure 3:
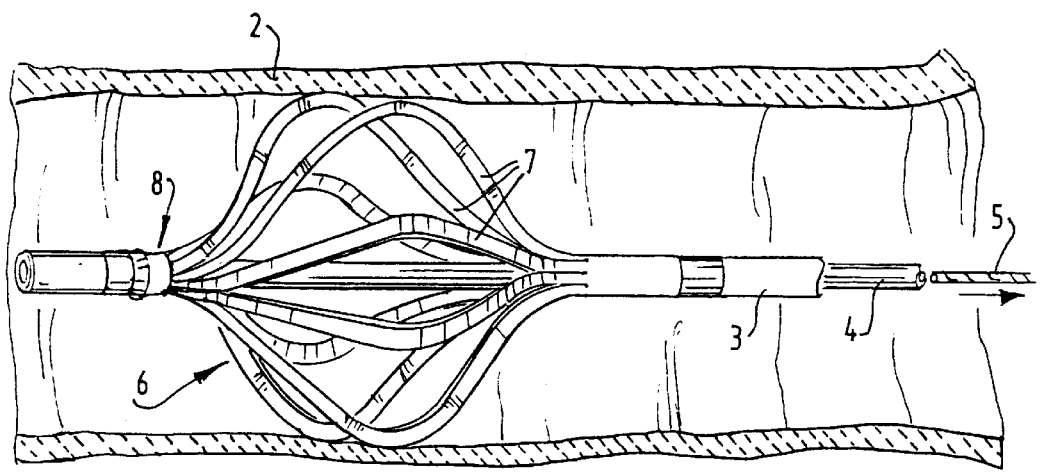
FIG. 3 illustrates the end of the catheter shown in FIG. 1 with the filter element unfolded.

FIG. 3 shows the unfolded, operative state of the filter element 6. This state is brought about when the catheter 1, and in particular the filter element 6, has been maneuvered in the target position inside the blood vessel 2. The guide wire 5 can then be removed.

In order to unfold the filter element 6, the inner tube-like body 4 is moved in relation to the outer tube-like body 3 in a proximal direction. As a result the ends of the strips 7 are moved towards each other, so that these strips bend outwards until they make contact with the wall of the blood vessel 2. The connecting means 8 retain the ends of the strips 7 in a reliable manner.

When the catheter is left inside the body with the filter element unfolded in this manner for a longer period of time, tissue 20 will start growing around strips 7 positioned against the wall of the blood vessel 2. The strips 7 form 'passages' as it were inside this tissue 20. The state in which the strips 7 have grown together with the tissue has been illustrated in FIG. 4. When in this situation the catheter would be removed just like that, the tissue grown around the strips 7 would have to be torn, with all the attendant risks.

With the catheter described here, the distal ends 10 of the strips 7 are detached from the connecting means 8 however before the catheter is removed.

Detaching the said distal ends is simply done by moving the inner tube-like element 4 in relation to the outer tube-like element 3 in a distal direction. The elastic sleeve 11 is then slid off the distal ends 10 of the strips 7, as a result of which these ends 10 are released in the manner illustrated in the FIGS. 5 and 6.

When the catheter is subsequently removed, the strips 7 will slide easily through the passages 21 formed inside the tissue 20, without any damage being done to this tissue 20. In other words, the catheter can be removed without problems and without trauma.

As can be seen in the FIGS. 2, 5 and 6, the ends 10 of the strips 7 are provided with a projection which ensures a good grip of the sleeve on the ends 10.

FIG. 7 shows a somewhat different embodiment of the strips 7, in which case the projections, indicated here with the reference number 25, are formed by a depression 24 in the outside surface of each strip 7 at a small distance from the distal end thereof. The depth of the depression 24 is equal to the thickness of the sleeve 11, so that the outside surface of the catheter with the strips 7 is even and smooth in the connected state.

The invention is not limited to the embodiment shown and described herein. Specifically the connecting means with which the relatively distal ends of the strips are connected with the basic body can be embodied in other ways than shown. The distal ends of the strips can be connected by adhesives, pre-cut areas, hooks, and so on and so forth. Also the end-section 14 can be formed such that it is directly connected to the elastic sleeve 11, so that end-section 14 and ring 4 and element 13 form one element.

I claim:

1. Filter catheter comprising: a tube-like catheter body with a proximal and a distal end; a filter element arranged at the catheter distal end, said filter element formed by a number of strips arranged spaced out around the circumference of the catheter body, and said strips having proximal and distal ends, and said strips connected to the catheter body at least at their distal ends wherein the distal ends of the strips are connected with the body by detachable connecting means; and wherein the distal ends of the strips comprise a projection from said strip.

2. Filter catheter as claimed in claim 1, wherein the catheter body comprises an outer tube-like body and an inner tube-like body removeably received inside the outer tube-like body, and said strips connected with their proximal ends to the outer tube-like body and with their distal ends to the inner tube-like body; and wherein the connecting means are placed on the inner body and retain the distal ends of the strips by means of a clamping connection.

3. Filter catheter as claimed in claim 2, wherein the connecting means comprise a sleeve connected to the inner tube-like body, said sleeve clamped around the distal ends of the strips.

4. Filter catheter as claimed in claim 3, wherein the sleeve has been made of an elastic material.

5. Filter catheter of claim 4 wherein the elastic material is silicone rubber.

6. Filter catheter comprising: a tube-like catheter body with a proximal and a distal end; a filter element arranged at the catheter distal end, said filter element formed by a number of strips arranged spaced out around the circumference of the catheter body, and said strips having proximal and distal ends, and said strips connected to the catheter body at least at their distal ends wherein the distal ends of the strips are connected with the body by detachable connecting means;

wherein the distal ends of the strips comprise a projection from said strip; and wherein the projection is formed by a wall section of said adjoining a depression in the outside surface of each strip, at a small distance from the distal end of the strip.

7. Filter catheter comprising: a tube-like catheter body with a proximal and a distal end; a filter element arranged at the catheter distal end, said filter element formed by a number of strips arranged spaced out around the circumference of the catheter body, and said strips having proximal and distal ends, and said strips connected to the catheter body at least at their distal ends wherein the distal ends of the strips are connected with the body by detachable connecting means;

wherein the catheter body comprises an outer tube-like body and an inner tube-like body removeably received inside the outer tube-like body, and said strips connected with their proximal ends to the outer tube-like body and with their distal ends to the inner tube-like body; and wherein the connecting means are placed on the inner body and retain the distal ends of the strips by means of a clamping connection; and wherein the distal ends of the strips comprise a projection from said strip.

* * * * *